(12) United States Patent
Harrah et al.

(10) Patent No.: US 9,198,746 B2
(45) Date of Patent: Dec. 1, 2015

(54) MATERIALS AND METHODS FOR SECURING BODILY IMPLANTS

(75) Inventors: Timothy P. Harrah, Cambridge, MA (US); Kenneth Daignault, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 87 days.

(21) Appl. No.: 13/595,545

(22) Filed: Aug. 27, 2012

(65) Prior Publication Data

US 2013/0225918 A1    Aug. 29, 2013

Related U.S. Application Data

(60) Provisional application No. 61/529,107, filed on Aug. 30, 2011.

(51) Int. Cl.
A61F 2/00 (2006.01)

(52) U.S. Cl.
CPC .............. *A61F 2/0009* (2013.01); *A61F 2/0036* (2013.01); *A61F 2/0063* (2013.01); *A61F 2/0077* (2013.01); *A61F 2250/0031* (2013.01)

(58) Field of Classification Search
CPC ................ A61F 2250/0031; A61F 2210/0076; A61F 2/0063; A61F 2/0045; A61L 31/048; A61L 31/16; A61L 31/148; A61L 23/06
USPC .......... 600/29–31, 37; 128/897, 898, DIG. 25
See application file for complete search history.

(56) References Cited

U.S. PATENT DOCUMENTS

| | | | |
|---|---|---|---|
| 4,292,972 A * | 10/1981 | Pawelchak et al. ........... 604/368 |
| 5,824,082 A | 10/1998 | Brown |
| 6,214,045 B1 * | 4/2001 | Corbitt et al. ..................... 623/8 |
| 6,669,706 B2 | 12/2003 | Schmitt et al. |
| 6,669,735 B1 | 12/2003 | Pelissier |
| 6,953,428 B2 | 10/2005 | Gellman et al. |
| 7,070,558 B2 | 7/2006 | Gellman et al. |
| 7,594,921 B2 * | 9/2009 | Browning ..................... 606/151 |
| 7,717,892 B2 | 5/2010 | Bartning et al. |
| 2003/0069469 A1 | 4/2003 | Li |
| 2005/0250978 A1 | 11/2005 | Kammerer |
| 2006/0282105 A1 | 12/2006 | Ford et al. |
| 2007/0088189 A1 | 4/2007 | Levy |
| 2007/0156012 A1 | 7/2007 | Tracey et al. |
| 2007/0276494 A1 | 11/2007 | Ferree |
| 2008/0161837 A1 | 7/2008 | Toso et al. |
| 2008/0215087 A1 * | 9/2008 | Pavcnik et al. ............... 606/213 |
| 2008/0281149 A1 | 11/2008 | Sinai et al. |
| 2009/0099579 A1 * | 4/2009 | Nentwick et al. ............. 606/151 |
| 2010/0081866 A1 | 4/2010 | Goddard et al. |
| 2013/0197300 A1 * | 8/2013 | Koullick et al. ................ 600/37 |

FOREIGN PATENT DOCUMENTS

| WO | 2007087146 A2 | 8/2007 |
| WO | 2008015722 A1 | 2/2008 |
| WO | 2009005714 A1 | 1/2009 |

* cited by examiner

*Primary Examiner* — Samuel Gilbert
(74) *Attorney, Agent, or Firm* — Brake Hughes Bellermann LLP (57) ABSTRACT

In one embodiment, a medical device includes a resorbable material that is configured to be disposed within the body of the patient proximate a bodily implant. The resorbable material is configured to frictionally retain the implant in place within the body of the patient for at least a period of time. In one embodiment, a kit includes an implant and a resorbable material. The implant is configured to be disposed within a body of a patient. The resorbable material is configured to be disposed within the body of the patient proximate the implant to frictionally retain the implant in place within the body of the patient for a period of time. The resorbable material is configured to be resorbed by the body after the period of time.

16 Claims, 5 Drawing Sheets

MATERIALS AND METHODS FOR SECURING BODILY IMPLANTS

CROSS REFERENCE TO RELATED APPLICATION

This application is a Nonprovisional of, and claims priority to, U.S. Provisional Application No. 61/529,107, filed on Aug. 30, 2011, entitled "MATERIALS AND METHODS FOR SECURING BODILY IMPLANTS", which is incorporated by reference herein in its entirety.

TECHNICAL FIELD

This disclosure relates generally to medical devices and more particularly to implants configured to provide support within a body of a patient and materials and methods for securing such implants within the body of the patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the implant used, pelvic floor repair can require various fixation locations within a pelvic region. For example, an implant can be secured using a number of fixation points.

In some implants, sutures may be used to bridge, anchor and suspend the implants in place within the body of the patient. In other implants, the implants include arm members or anchors that extend to and couple to bodily tissue to suspend or retain the implant in place within the body of the patient. As tissue in-growth occurs on the implants, however, the sutures, arms, or other anchoring members may no longer be necessary to retain the implant in place within the body of the patient. The tissue in-growth may support the implant within the body such that the sutures, arm members, and other anchor members are pulled from their anchor locations. This pulling within the body of the patient may be painful and/or harmful to the body of the patient.

Accordingly, it is desirable to provide an implant that does not include specific fixation points within the body of the patient. Additionally, it is desirable to provide an implant and a securement mechanism that allows the implant to be secured within the body of the patient for a period of time (for example, while the tissue in-growth is occurring).

SUMMARY

In one embodiment, a medical device includes a resorbable material that is configured to be disposed within the body of the patient proximate a bodily implant. The resorbable material is configured to frictionally retain the implant in place within the body of the patient for at least a period of time. In one embodiment, a kit includes an implant and a resorbable material. The implant is configured to be disposed within a body of a patient. The resorbable material is configured to be disposed within the body of the patient proximate the implant to frictionally retain the implant in place within the body of the patient for a period of time. The resorbable material is configured to be resorbed by the body after the period of time.

DETAILED DESCRIPTION

The devices and methods described herein are generally directed to bodily implants. For example, in some embodiments the implants are configured to be placed in the pelvic region of the patient. For example, the implant may be a posterior support implant, an anterior support implant, a total pelvic floor repair implant, an incontinence sling implant. An implant can be placed into the pelvic space of a male or female patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures as desired. A procedure to deploy a pelvic implant can include vaginal incisions, such as an anterior vaginal incision and/or a posterior vaginal incision.

Figure 1:
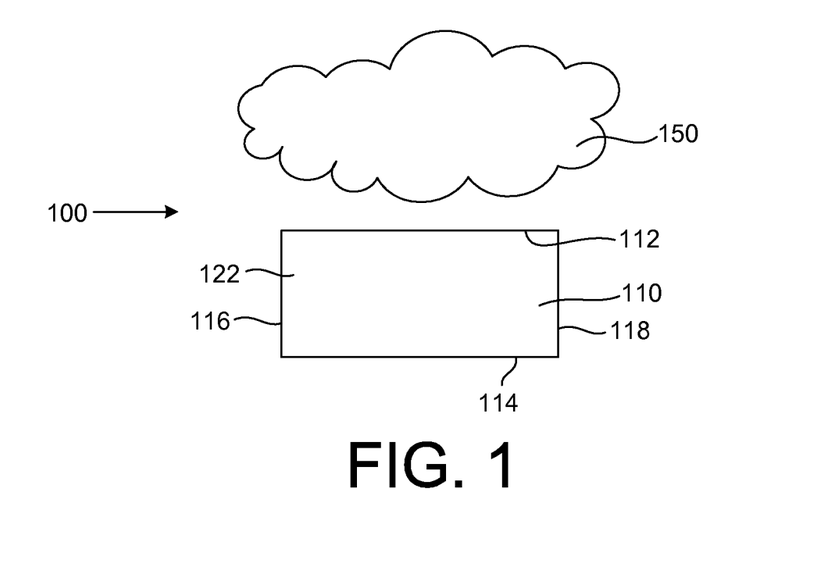
FIG. 1 is a schematic illustration of a kit according to an embodiment of the invention.

FIG. 1 is a schematic illustration of a medical device 100 according to an embodiment of the invention. The medical device 100 includes an implant 110 and a material 150.

In some embodiments, the implant 110 is configured to be placed and secured within a body of a patient. The implant 110 is configured to provide support to a portion of the body. For example, in some embodiments, the implant 110 may be placed and secured proximate the bladder of the patient to provide support to the bladder of the patient. In other embodiments, the implant 110 is configured to be placed and secured proximate the uterus of the patient to provide support to the uterus of the patient. In further embodiments, the implant 110 is configured to be placed and secured at other locations within the body of the patient.

The implant 110 may be of any shape and size. In some embodiments, the implant 110 is shaped to be inserted into a body of a patient and provide support for a portion of the body of the patient. For example, in some embodiments, the implant 110 is square. In other embodiments, the implant 110 is rectangular. In yet further embodiments, the implant 110 is round or oval.

In some embodiments, the implant 110 includes a top edge 112, a bottom edge 114, a first side edge 116, and a second side edge 118. The implant 110 also includes an upper surface 122 and a lower surface (not illustrated) opposite the upper surface 122.

The implant 110 may be formed of any biocompatible material or materials. In some embodiments, the implant 110 is formed of a mesh material. For example, the implant 110 may be formed of Advantage® mesh or the Polyform™ synthetic mesh, both as sold by Boston Scientific Corporation. In some embodiments, in the implant 110 may be formed of a polymer material. In some embodiments, the implant 110 is made of polypropylene. In some embodiments, the mesh material of the implant 110 allows for and/or promotes tissue in-growth to secure the implant 110 to the bodily tissue of the patient.

In some embodiments, the implant 110 is formed of a natural or non-synthetic material. For example, in some embodiments, the implant 110 is formed from bovine Xenform® as sold by Boston Scientific Corporation or cadaveric tissue Repliform® (human dermic) as sold by Boston Scientific Corporation.

In some embodiments, the implant 110 is formed of a multiple materials. For example, in some embodiments, a first portion of the implant 110 is formed of a synthetic material and a second portion of the implant 110 is formed of a natural material.

The material 150 is configured to be disposed within the body of the patient and help retain the implant 110 in place within the body of the patient.

In some embodiments, the material 150 is configured to retain the implant 110 in place within the body of the patient until the implant 110 is supported or retained in place by the body itself. For example, in some embodiments, the material 150 is configured to retain the implant in place within the body of the patient until the implant 110 undergoes tissue ingrowth (or tissue ingrowth occurs on the implant 110).

In some embodiments, the material 150 is biocompatible and biodegradable. For example, in some embodiments, the material 150 is a resorbable material and is configured to be resorbed or otherwise broken down and absorbed by the body of the patient. Accordingly, the material 150 can be placed within the body of the patient proximate the implant 110 to retain the implant 110 in place within the body of the patient for a period of time (for example, until the material is resorbed). For example, in some embodiments, the material 150 is configured to retain the implant 110 in place within the body of the patient until scarring, scar material, or tissue ingrowth occurs on the implant 110 to retain the implant 110 in place within the body of the patient. Once the scarring, scar material, or tissue ingrowth occurs on the implant 110, the implant 110 may be sufficiently retained within the body of the patient and the material 150 is resorbed by the body of the patient.

For example, in some embodiments, the material 150 is configured to retain the implant 110 in place within the body of the patient for a few days. Specifically, in some embodiments, the material 150 is configured to retain the implant 110 within the body of the patient for a period of 3 to 7 days. After the period of time, the scarring or tissue ingrowth on the implant 110 will help retain the implant 110 in place and positioned within the body of the patient.

In some embodiments, the material 150 is a foam material. For example, in some embodiments, the foam material is configured to be placed within the body of the patient in a first, compressed state and is configured to expand to a second state once the foam material is placed within the body of the patient. In other words, the volume of the foam material increases when the foam material is placed within the body of the patient. For example, in some embodiments, the foam material may be stored or retained outside of the body of the patient under a pressure (for example, in a pressurized container) to keep the foam material in its first, compressed state. Once the foam material is disposed within the body of the patient, the removal of the pressure (or the lower pressure of the body against the foam material) allows the foam material to expand to its second state or configuration.

In some embodiments, the material 150 helps to eliminate open areas in the body of the patient proximate the implant 110. In such embodiments, the material 150, for example, may help prevent blood or fluid accumulation proximate the implant 110. In some such embodiments, the material 150 may help prevent mesh erosion.

The material 150 may be any biocompatible material configured to help retain the implant in place within the body of the patient for a period of time. For example, in some embodiments, the material 150 includes alginate, collagen, poly(lactic-co-glycolic acid) (PLGA), or another polysaccharide. In other embodiments, the material 150 includes another type of biodegradable or resorbable material. In some embodiments, the material 150 is bioabsorbable.

In some embodiments, the material 150 includes an additive that provides a benefit or supplement to the body of the patient. For example, in some embodiments, the material 150 includes alginate and an additive. In some embodiments, the material 150 includes collagen, PLGA, or another polysaccharide and an additive. In some embodiments, the material includes more than one additive.

For example, in some embodiments, the material 150 includes additives to facilitate the placement of a large volume of additives into the body of the patient. For example, in some embodiments, the material 150 includes an additive such as an antibiotic. For example in some embodiments, the material 150 includes minocycline, tetracycline, or rifampicin. In other embodiments, the material 150 includes an additive such as an anti-inflammatory, such as, but not limited to, ketorolac or naproxen.

In some embodiments, the material 150 includes a trophic factor, such as tropic factors to recruit cells to produce ligamentous tissue or to stimulate cells to regulate collagen deposition. For example, in some embodiments, the trophic factors include members of the Transforming Growth Factor beta family (TGFb), the Fibroblast Growth Factor family (FGF) and the Bone Morphogenic Protein family (BMP).

In some embodiments, the material 150 includes an active pharmaceutical ingredient. In some embodiments, the material 150 includes stem cells. In other embodiments, the material 150 includes a material or substance that is configured to promote tissue ingrowth on the implant 110.

In some embodiments, the additives may also be grafted or otherwise disposed on the implant 110, for example, in areas where additional collagen production is desired.

In some embodiments, the material 150 is configured such that the material 150 may provide a support or scaffold to the body of the patient. In some such embodiments, tissue, such as prolapsed tissue, may be secured to the material either by sutures, adhesives, or by tissue in-growth.

In use the implant 110 may be inserted into a body of a patient. For example, in some embodiments, the implant 110 is inserted into a body of a patient through a vaginal incision such as an anterior or posterior vaginal incision. In other embodiments, the implant 110 is placed or disposed within the body of the patient through a different bodily incision or opening.

In some embodiments, the implant 110 is positioned within the body of the patient such that the implant 110 may provide support to a portion of the body of the patient. For example, in some embodiments, the implant 110 is placed proximate a bladder, a bladder neck, or a urethera of a patient and is configured to provide support to such portion of the body of the patient. In other embodiments, the implant 110 is placed or positioned proximate another portion or organ of the body of the patient and is configured to provide support to such bodily portion.

The material 150 may then be inserted or disposed within the body of the patient. In some embodiments, the material 150 is inserted into the body of the patient through the same bodily incision or opening that the implant 110 was inserted into the body through. In other embodiments, the material 150 is inserted into the body of the patient through a bodily incision or opening different than the incision or opening that was used to insert the implant 110 into the body of the patient. In some embodiments, the material 150 is inserted into the body of the patient using an insertion tool, such as a syringe. In other embodiments, the material may be inserted into the body of the patient using another insertion tool.

In some embodiments, the material 150 is inserted into the body proximate the implant 110. For example, in some embodiments, the material 150 is configured to contact the implant 110 (such as the upper surface 122 and/or the lower surface of the implant 110). In some embodiments, the material 150 is configured to be disposed within the body of the patient such that it extends from one end portion of the implant 110 to another end portion of the implant 110. In some embodiment, the material 150 is configured to be disposed within the body of the patient such that it substantially surrounds the implant 110. In other words, in some embodiments, the material is configured to be disposed within the body of the patient such that it extends along both the upper surface 122 and the lower surface of the implant 110 from one end portion of the implant 110 to the opposite end portion of the implant 110.

In some embodiments, the material is configured to mechanically support the implant 110 within the body of the patient. For example, in some embodiments, the material 150 is configured to be disposed within the body of the patient proximate the implant 110 and is configured to apply a pressure or a force against the implant 110 to frictionally couple the implant within the body of the patient. For example, in some embodiments, the material 150 is configured to apply a pressure or a force against the implant 110 to pressure or force the implant 110 against bodily tissue to frictionally couple the implant 110 to the bodily tissue (or to the material 150 itself).

In some embodiments, the material 150 may be disposed within the body of the patient in empty space of the body proximate the implant 110. Empty space is the space within the body of the patient that is not occupied by bodily organs, bones, or other portions of the body of the patient. Accordingly, the material 150 may be placed within the empty space of the body of the patient proximate the implant 110 to help prevent the implant 110 from moving within the empty space of the patient. In some embodiments, the material 150 is inserted into the patient until the material entirely fills the empty space of the patient proximate the implant 110. In other embodiments, the material 150 is configured to fill about 50% of the empty space of the patient proximate the implant 110. In other embodiments, the material 150 is configured to fill more than 50% of the empty space proximate the implant 110. In yet further embodiments, the material 150 is configured to fill less than 50% of the empty space proximate the implant 110.

In some embodiments, the medical device 100 is used in conjunction with a pessary. The pessary may be inserted into the vagina or rectum of the patient to help retain the implant in place within the body of the patient. For example, in some embodiments, the implant 110 is inserted into a pelvic region of the patient and a pessary is placed within the vagina of the patient after the implant has been inserted and positioned within the body. The pessary may be configured to retain the vagina in an expanded position or configuration and apply a force against the implant 110 to maintain the position of the implant within the body of the patient.

In some embodiments, the pessary may be used after the implant 110 and material 150 have been placed within the body of the patient. In other embodiments, the pessary is used and placed within the body of the patient after only the implant 110 has been placed within the body of the patient.

Figure 2A:
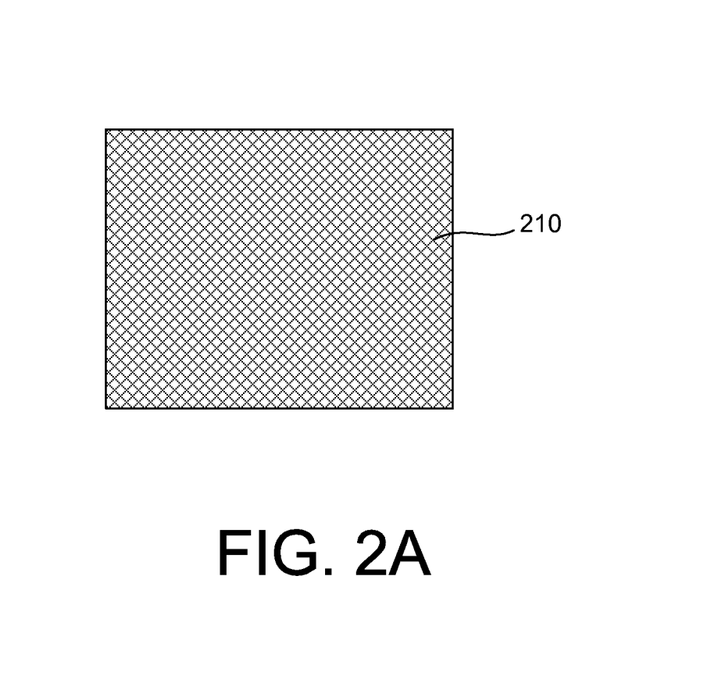
FIGS. 2A-2D are top views of implants according to embodiments of the invention.
Figure 2B:
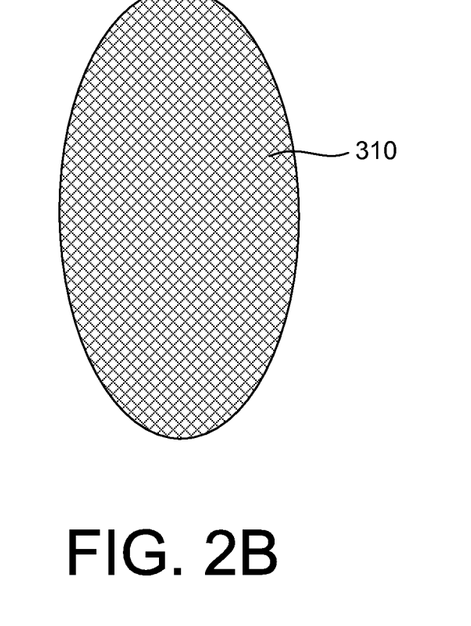
Figure 2C:
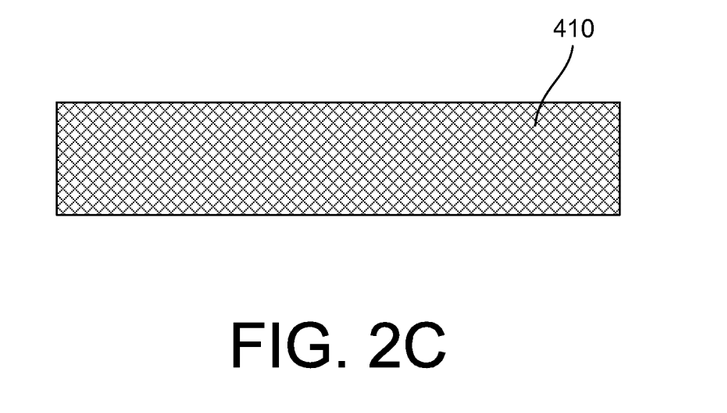
Figure 2D:
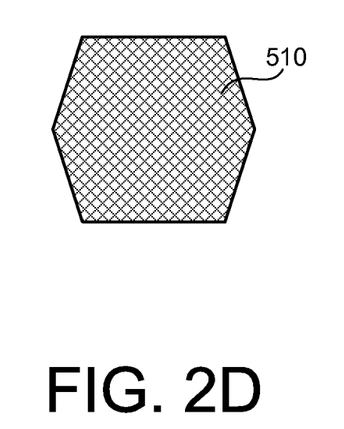

FIGS. 2A-2D are top views of various implants according to embodiments of the invention. As illustrated in FIG. 2A, the implant 210 may have a generally square shape. As illustrated in FIG. 2B, the implant 310 may have a generally circular or oval shape. As illustrated in FIG. 2C, the implant 410 may have a generally rectangular shape. As illustrated in FIG. 2D, the implant 510 may have an irregular shape.

In some embodiments, the material may be inserted into a body of a patient using an insertion tool. For example, a syringe may be used to insert the material 150 into the body of the patient.

Figure 3:
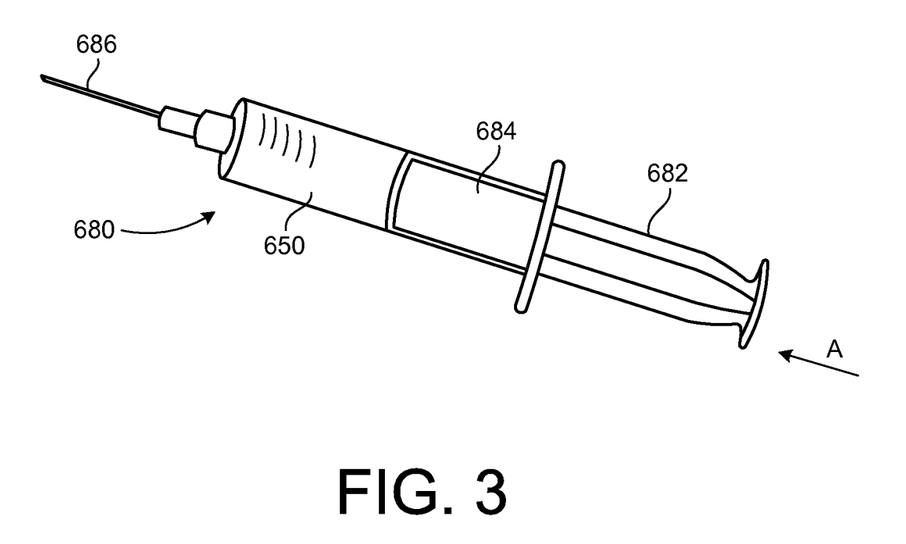
FIG. 3 is an insertion tool filled with a resorbable material according to an embodiment of the invention.

FIG. 3 is a perspective view of an insertion tool 680 containing a material 650. The insertion tool includes a reservoir 684 and a needle portion 686. The insertion tool 680 may be used to insert, advance, or otherwise dispose the material 650 into the body of the patient. For example, in some embodiments, the insertion tool 650 may be used to insert the material 650 into the body of a patient through a vaginal incision. In other embodiments, the insertion tool 680 may be used to insert the material into the body of the patient through another incision or opening of the body.

In the illustrated embodiment, the insertion tool 680 includes a plunger or actuator 682 that may be advanced or activated to eject the material 650 from the reservoir 684 of the insertion tool 680, through the needle portion 686 of the insertion tool 680, and into the body of the patient. For example, in the illustrated embodiment, the plunger or actuator 682 may be advanced in the direction of arrow A to eject the material 650 from the insertion tool 680.

In some embodiments, the insertion tool 680 is configured to retain the material 650 in a compressed state or configuration. For example, in some embodiments, the insertion tool 680 is configured to apply or retain a pressure on the material 650 to retain the material 650 in a compressed state or configuration. For example, in some embodiments, the reservoir 684 is configured to apply pressure to the material 650 to retain the material 650 in its compressed state or configuration.

Figure 4:
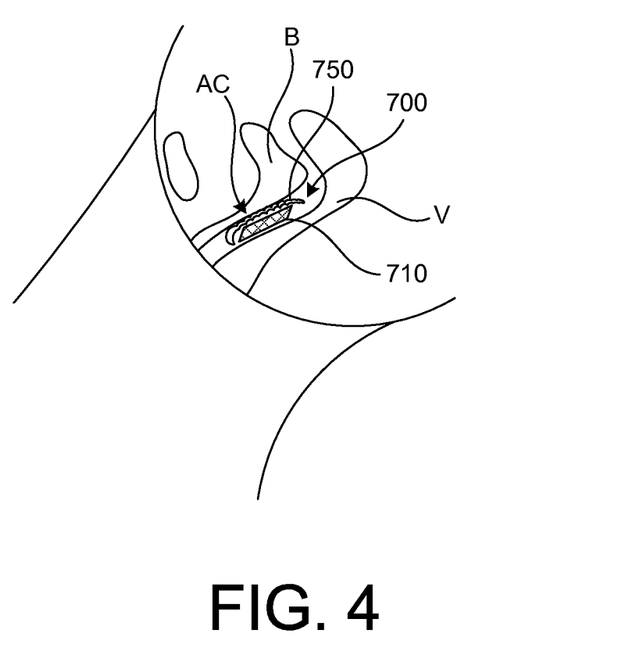
FIG. 4 is a schematic illustration of an implant and a resorbable material disposed within a body of a patient according to an embodiment of the invention.

FIG. 4 is a schematic illustration of a medial device 700 disposed within a body of a patient. In the illustrated embodiment, the implant 710 is disposed between a bladder B and a vagina V of the patient. The implant 710 is configured and positioned to provide support to the bladder B of the patient.

Figure 5:
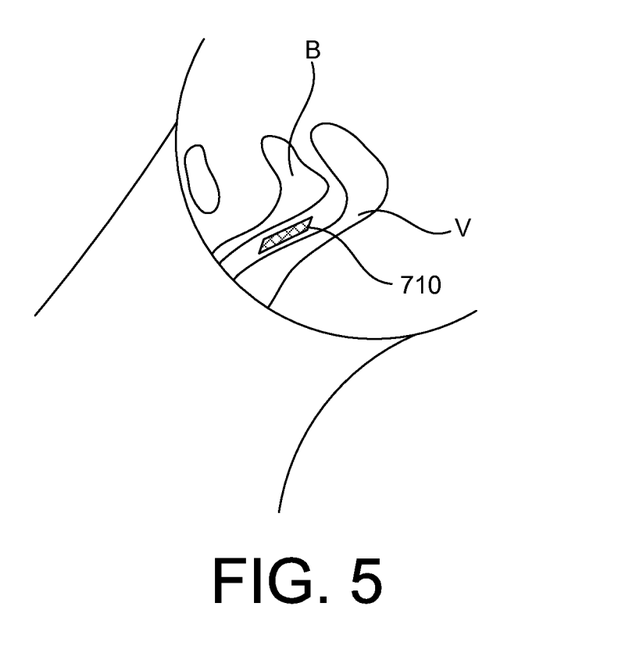
FIG. 5 is a schematic illustration of an implant disposed within a body of a patient according to an embodiment of the invention.

The material 750 is disposed within the anterior compartment AC (such as the empty space of the anterior compartment AC). In some embodiments, the material 750 is disposed within the body of the patient such that the material 750 surrounds the implant 710. The material 750 is configured to retain the implant 710 in place and positioned within the body of the patient until scarring or tissue ingrowth occurs on the implant 710. For example, in some embodiments, once the scarring or tissue ingrowth occurs the material 750 is resorbed by the body of the patient and the implant 710 remains in place within the body of the patient (as illustrated in FIG. 5).

Figure 6:
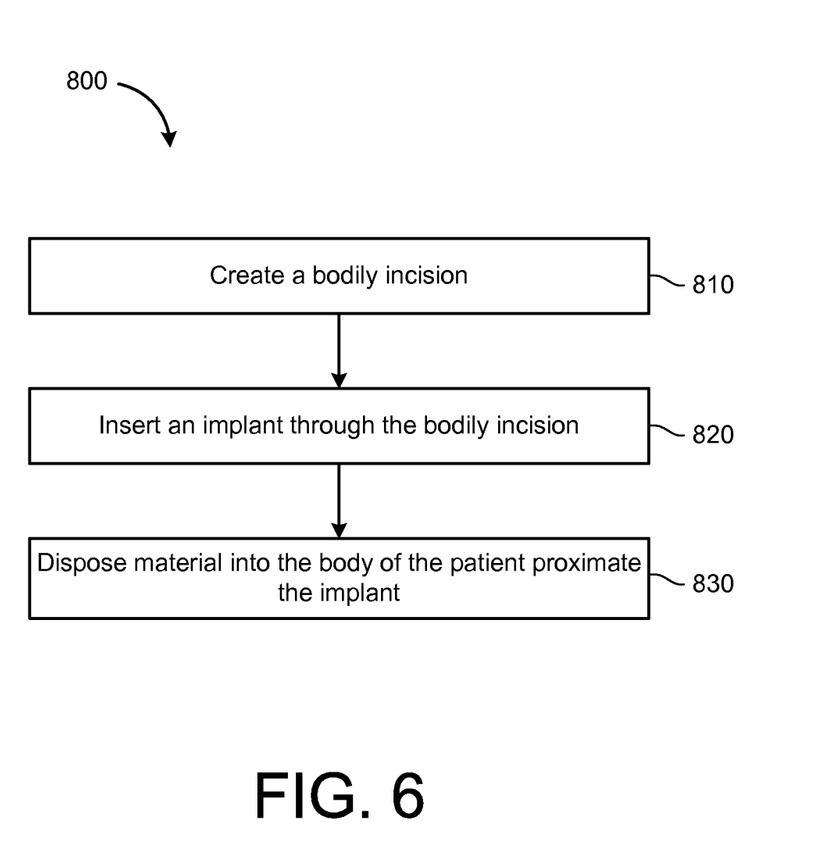
FIG. 6 is a flow chart of a method according to an embodiment of the invention.

FIG. 6 is a flow chart that illustrates a method 800 for placing a medical device within a body of a patient. In one embodiment, the method 800 includes creating a bodily incision or opening (810). In some embodiments, the creating a bodily incision or opening (810) includes creating a vaginal incision. For example, in some embodiments, an anterior vaginal incision is created. In other embodiments, a posterior vaginal incision is created.

In some embodiments, the method includes inserting an implant through the bodily incision (820). For example, in some embodiments, the implant is inserted into the body of the patient through an anterior vaginal incision. In other embodiments, the implant is inserted through a posterior vaginal incision. In yet a further embodiment, the implant is inserted through a different bodily incision.

In some embodiments, the implant is inserted into the body of the patient such that the implant is positioned to provide support to a portion of the body of the patient. For example, in some embodiments, the implant is positioned within the body such that the implant is configured to provide support to a bladder, a bladder neck, or a urethra of the patient. In other embodiments, the implant is positioned within the body such that the implant is configured to provide support to a uterus, rectum or other portion of the body of the patient in the pelvic region of the patient. In yet a further embodiment, the implant is positioned within the body such that the implant is configured to provide support to another portion or organ of the body of the patient.

In some embodiments, the method includes disposing a material into the body of the patient proximate the implant to frictionally couple the implant in place within the body of the patient (830). In some embodiments, the material is disposed within the body of the patient such that the implant is frictionally coupled implant in place within the body of the patient for a period of time. For example, in some embodiments, the material is configured to be resorbed by the body of the patient and is disposed within the body such that the implant is coupled in place within the body of the patient for 3 to 7 days. In other embodiments, the material is configured to be disposed within the body of the patient such that the implant is coupled in place for a period of time longer than 7 days. In some embodiments, the material is configured to remain within the body to retain the implant in place within the body of the patient for a time sufficient for scarring or ingrowth to occur on the implant.

In some embodiments, the material is inserted or disposed within the body of the patient through a bodily incision or opening. In some embodiments, the material is inserted or disposed within the body of the patient through the same incision that is used to insert the implant within the body of the patient. In other embodiments, the material is inserted into the body of the patient through an incision or opening that is different than the incision or opening that is used to insert the implant into the body of the patient.

In some embodiments, the material is inserted or disposed within the body of the patient using an insertion tool. For example, in some embodiments, a syringe is used to insert or dispose the material into the body of the patient.

In some embodiments, the material is disposed within the body of the patient such that the material is configured to force the implant against bodily tissue surrounding the implant to frictionally couple the implant in place within the body of the patient. In some embodiments, the material is disposed within the body of the patient such that the implant is compressed or forced against bodily tissue to frictionally couple the implant within the body of the patient. In some embodiments, the material is disposed within the body of the patient such that the material substantially surrounds the implant to frictionally retain the implant within the body of the patient. For example, in such embodiments, a portion of the material is disposed between implant and the bodily tissue and the implant is compressed or forced against the material (and the bodily tissue) to frictionally couple the implant within the body of the patient (for example, to the bodily tissue).

In some embodiments, only a portion of the implant is forced or frictionally coupled within the body of the patient. For example, in some embodiments, only an end portion of the implant is contacted by the material and forced against bodily tissue to couple the implant within the body of the patient. In other embodiments, the entire implant is frictionally coupled or forced against bodily tissue to couple the implant in place within the body of the patient.

In some embodiments, the material is disposed within the body of the implant in a compressed, first state or configuration. The material is allowed to expand to a second state or configuration once it is within the body of the patient. For example, in some embodiments, the material is a foam material that is configured to expand once it is placed within the body of the patient.

In some embodiments, the material is disposed within an empty space of the body of the patient. For example, in some embodiments, the material is disposed within a space of the body of the patient that is generally empty (i.e., does not include other organs or bone structure of the patient). In some embodiments the material is disposed within the body of the patient such that about half or more than half of the empty space proximate the implant is filled with the material.

In some embodiments, a medical device includes a resorbable material configured to be disposed within the body of the patient proximate a bodily implant. The resorbable material is configured to frictionally retain the implant in place within the body of the patient for at least a period of time.

In some embodiments, the resorbable material includes at least one of a group consisting of an antibiotic, stem cells, and a trophic factor. In some embodiments, the resorbable material is a foam material. In some embodiments, the resorbable material is a foam material and is configured to be inserted into the body of the patient in a first state and is configured to expand to a second state while disposed within the body of the patient. In some embodiments, the resorbable material is configured to be disposed in an empty space of the body of the patient proximate the implant and apply a force against the implant to frictionally couple the implant to bodily tissue for the period of time.

In some embodiments, a kit includes an implant and a resorbable material. The implant is configured to be disposed within a body of a patient. The resorbable material is configured to be disposed within the body of the patient proximate the implant to frictionally retain the implant in place within the body of the patient for a period of time. The resorbable material is configured to be resorbed by the body after the period of time.

In some embodiments, the resorbable material includes at least one of the group consisting of an antibiotic, stem cells, and a trophic factor. In some embodiments, the resorbable material is a foam material. In some embodiments, the resorbable material is a foam material and is configured to be inserted into the body of the patient in a first state and is configured to expand to a second state while disposed within the body of the patient. In some embodiments, the resorbable material is configured to be disposed in an empty space of the body of the patient proximate the implant and apply a force against the implant to frictionally couple to bodily tissue for the period of time.

In some embodiments, the implant is formed of a mesh material. In some embodiments, the implant is configured to receive tissue growth thereon. In some embodiments, the implant is configured to receive tissue growth thereon to help retain the implant in place within the body of the patient at a time after the period of time.

In some embodiments, a method of placing an implant within a body of a patient includes (1) inserting the implant into the body of the patient, and (2) disposing a material into the body of the patient proximate the implant to frictionally couple the implant in place within the body of the patient for at least a period of time.

In some embodiments, the disposing a material includes disposing the material within the body of the patient such that implant is forced against bodily tissue surrounding the implant. In some embodiments, the disposing a material includes disposing the material within empty space of the body proximate the implant.

In some embodiments, the method includes creating a vaginal incision and the inserting the implant includes inserting the implant through the vaginal incision.

In some embodiments, the method includes creating a vaginal incision and the inserting the implant includes inserting the implant through the vaginal incision such that that the implant is positioned to provide support to a portion of the body of the patient.

In some embodiments, the disposing includes disposing a resorbable material into the body of the patient. In some embodiments, the inserting includes inserting an implant that is configured to receive tissue ingrowth thereon.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   a mesh implant having a first surface and a second surface, the mesh implant being configured to provide support to a portion of a body of a patient in a pelvic region of the patient; and
   a resorbable foam material configured to be disposed within the body of the patient proximate the mesh implant, the resorbable material being configured to frictionally retain the first surface of the implant in place on the portion of the body of the patient for at least a period of time by applying a force against the second surface of the implant.

2. The medical device of claim 1, wherein the resorbable material includes at least one of a group consisting of an antibiotic, stem cells, and a trophic factor.

3. The medical device of claim 1, wherein the resorbable foam material is configured to be inserted into the body of the patient in a compressed state and is configured to expand to an expanded state when disposed within the body of the patient.

4. The medical device of claim 1, wherein the resorbable foam material is configured to be disposed in an empty space of the body of the patient proximate the implant to apply the force against the second surface of the implant to frictionally retain the first surface of the implant on the portion of the body of the patient for the at least the period of time.

5. A kit, comprising:
   a mesh implant configured to be disposed within a body of a patient and provide support to a portion of the body of the patient in a pelvic region; and
   a resorbable foam material configured to be disposed within the body of the patient proximate the implant at a time after disposing the implant within the body of the patient, the resorbable material further configured to assert a force on the mesh implant to frictionally retain the mesh implant in place on the portion of the body of the patient for a period of time, the resorbable material being configured to be resorbed by the body after the period of time.

6. The kit of claim 5, wherein the resorbable material includes at least one of the group consisting of an antibiotic, stem cells, and a trophic factor.

7. The kit of claim 5, wherein the resorbable foam material is configured to be inserted into the body of the patient in a first state and is configured to expand to a second state while disposed within the body of the patient.

8. The kit of claim 5, wherein the resorbable foam material is configured to be disposed within the body of the patient by delivery through a needle.

9. The kit of claim 5, wherein the implant is configured to receive tissue growth thereon.

10. The kit of claim 5, wherein the implant is configured to receive tissue growth thereon to help retain the implant in place within the body of the patient at a time after the period of time.

11. A method comprising:
    inserting a mesh implant into a body of a patient, the mesh implant being inserted such that a first surface of the mesh implant is in contact with a portion of the body of the patient in a pelvic region; and
    disposing, after the inserting, an expandable resorbable material into the body of the patient proximate the mesh implant to frictionally retain the first surface of the mesh implant in place on the portion of the body of the patient for at least a period of time by applying a force against a second surface of the mesh implant.

12. The method of claim 11, wherein the disposing the expandable resorbable material includes disposing the expandable resorbable material within the body of the patient such that the mesh implant is forced against bodily tissue contacting the first surface of the implant.

13. The method of claim 11, wherein the disposing the expandable resorbable material includes disposing the expandable resorbable material within an empty space of the body of the patient proximate the implant.

14. The method of claim 11, further comprising:
    creating a vaginal incision,
    the inserting the implant including inserting the implant through the vaginal incision.

15. The method of claim 11, further comprising:
creating a vaginal incision,
the inserting the implant including inserting the implant through the vaginal incision such that that the implant is positioned to provide support to the portion of the body of the patient.

16. The method of claim 11, wherein the inserting includes inserting an implant that is configured to receive tissue ingrowth thereon.

* * * * *